(12) United States Patent
Guerra et al.

(10) Patent No.: US 8,907,125 B2
(45) Date of Patent: Dec. 9, 2014

(54) PREPARATION OF PERFLUOROVINYL ETHER SULFINIC ACIDS AND THEIR SALTS

(75) Inventors: Miguel A. Guerra, Woodbury, MN (US); Tatsuo Fukushi, Woodbury, MN (US); Zai-Ming Qiu, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 13/994,967

(22) PCT Filed: Dec. 13, 2011

(86) PCT No.: PCT/US2011/064557
§ 371 (c)(1),
(2), (4) Date: Jun. 17, 2013

(87) PCT Pub. No.: WO2012/082695
PCT Pub. Date: Jun. 21, 2012

(65) Prior Publication Data
US 2013/0267732 A1    Oct. 10, 2013

Related U.S. Application Data

(60) Provisional application No. 61/424,138, filed on Dec. 17, 2010.

(51) Int. Cl.
*C07F 9/22* (2006.01)
*C07C 313/02* (2006.01)
*C07C 313/04* (2006.01)

(52) U.S. Cl.
CPC ............. *C07C 313/02* (2013.01); *C07C 313/04* (2013.01)
USPC ........................................................ 562/22

(58) Field of Classification Search
None
See application file for complete search history.

(56) References Cited

U.S. PATENT DOCUMENTS

| | | | | |
|---|---|---|---|---|
| 3,420,877 A | * | 1/1969 | Pavlik | 562/125 |
| 3,919,301 A | | 11/1975 | Roesky et al. | |
| 4,544,458 A | | 10/1985 | Grot et al. | |
| 4,626,553 A | * | 12/1986 | Hane et al. | 521/27 |
| 5,285,002 A | * | 2/1994 | Grootaert | 526/222 |
| 5,639,837 A | * | 6/1997 | Farnham et al. | 526/222 |
| 6,462,228 B1 | * | 10/2002 | Dams | 562/125 |
| 2004/0247548 A1 | | 12/2004 | Haring et al. | |

FOREIGN PATENT DOCUMENTS

| | | |
|---|---|---|
| JP | S552-24176 A | 2/1977 |
| JP | 2006131588 | 5/2006 |
| WO | WO 03/010647 A2 | 2/2003 |

OTHER PUBLICATIONS

Burdon et al., Journal of the Chemical Society, Jun. 1, 1957, pp. 2574-2578.*
Fan-Hong et al., "Studies on sulfinatodehalogenation. XXIX. The sulfinatodehalogenation of primary polyfluoroalky iodides and bromides by sodium disulfite", Journal of Fluorine Chemistry, vol. 67, 1994, pp. 233-234.
Hu et al., "Reaction of Perfluoroalkanesulfinates with Allyl and Propargyl Halides, A Convenient Synthesis of 3-(Perfluoroalkyl) prop-1-enes and 3-(Perfluoroalkyl)allenes", Journal of Organic Chemistry, vol. 56, 1991, pp. 2801-2804.
Hu et al., "Photooxidation of Perhalofluorosulfinates. A Simple and Effective Method for the Synthesis of Perhalofluorocarboxylic Acids and Their Esters from the Corresponding Sulfonyl Fluorides", Journal of Fluorine Chemistry, vol. 42, 1989, pp. 145-148.
Huang et al., "Perfluoroalkylation initiated with sodium dithionite and related reagent systems", Journal of Fluorine Chemistry, vol. 58, 1992, pp. 1-8.
Huang et al., "Studies on Sulfinatodehalogenation, IV. The sulfinatodebromination of primary perfluoroalkyl bromides and perfluoroalkylene α 107-dibromides", Acta Chimica Sinica, No. 1, 1986, pp. 68-72.
Huang et al., "Studies on Sulfinatodehalogenation, VIII. Sodium dithionite-initiated perfluoroalkyl radical addition on double bond", Acta Chimica Sinica, No. 2, 1986, pp. 178-184.
Burdon, J. et al., "Fluorinated Sluphonic Acids. Part I., Perfluoromethane-,-octane-, and —decane-sulphonic Acids and their Simple Derivatives", Journal of the Chemical Society, Chemical Society, Letchworth; GB, Jun. 1, 1957, pp. 2574-2578.
Supplementary European Search Report for application No. EP 11 84 8728, dated Apr. 9, 2014, 6 pages.

* cited by examiner

*Primary Examiner* — Karl J Puttlitz
(74) *Attorney, Agent, or Firm* — C. Michael Geise

(57) ABSTRACT

There is provided a process for preparing a perfluorovinyl ether sulfinate, comprising: a) providing a perfluorovinyl ether sulfonyl halide; and (b) reducing the perfluorovinyl ether sulfonyl halide with a reducing agent in an organic protic solvent.

12 Claims, No Drawings

PREPARATION OF PERFLUOROVINYL ETHER SULFINIC ACIDS AND THEIR SALTS

The present invention relates to methods of making monomeric perfluorovinyl ether sulfinic acids and salts thereof.

BACKGROUND

Perfluorovinyl ether sulfinic acids and salts thereof have utility as initiators in free radical polymerization reactions.

Methods for the synthesis of fluorochemical sulfinates have been reported in the literature. For example, perfluoroalkane sulfinates can be prepared from the corresponding perfluoroalkanehalides via a dehalogenation and sulfination reaction using a sulfite plus an oxidant, hydroxymethane sulfinate, thiourea dioxide or sodium dithionite in water and such cosolvents as acetonitrile, glycol, diethylene glycol and alcohols.

Fluorocarbon sulfinates can also be prepared by reduction of the corresponding perfluoroalkane sulfonyl halides using sulfites, hydrazine, dithionites, and zinc in solvents such as dioxane, dimethoxyethane, di-n-butyl ether, tetrahydrofuran (THF), and diethylene glycol diethyl ether. These methods are reported in U.S. Pat. No. 3,420,877; U.S. Pat. No. 5,285,002 (Grootaert); U.S. Pat. No. 5,639,837 (Farnham et al.); U.S. Pat. No. 6,462,228 (Dams); Japanese Laid Open Patent Publication No. 2006131588 (Aoki); WO 03/10647 (Moll); C. M. Hu, F. L. Quing and W. Y. Huang, *J Org Chem*, 1991, 2801-2804; W. Y. Huang, *Journal of Fluorine Chemistry*, 58, 1992, 1-8; W. Y. Huang, B. N. Huang and W. Wang in *Acta Chim. Sinica (Engl. Ed.)*, 1986, 178-184, and *Acta Chim. Sinica (Engl. Ed.)*, 1986, 68-72; F. H. Wu and B. N. Huang, *Journal of Fluorine Chemistry*, 67, 1994, 233-234; C. M. Hu, F. L. Quing and W. Y. Huang, *Journal of Fluorine Chemistry*, 42, 1989, 145-148.

For some functionalized starting materials, these methods present several disadvantages, including slow reaction times, large amounts of by-products which typically must be removed from the sulfinate and required use of a cosolvent that may have a negative impact on processes in which the sulfinate is ultimately employed, e.g., free-radical polymerization reactions.

Polymeric fluorosulfinates have also been synthesized by utilizing methods such as reduction of fluorosulfonyl halide polymer side chains and dehalogenation and sulfination of alkyl halide polymer side chains, as reported in U.S. Pat. No. 4,544,458 (Grot et al.) and Japanese Patent No. 52-24176 (Seko et al.).

Although some functionalized polymeric sulfinates have been synthesized with conventional methods, conventional methods of synthesizing the corresponding monomeric functionalized perfluoroalkyl sulfinates have resulted in poor yields and numerous by-products that require additional separation and purification steps. See, for example, U.S. Pat. No. 5,639,837 (Farnham et al.).

Accordingly, there continues to be a need for an improved process for preparing fluorinated sulfinates, particularly functionalized fluorinated sulfinates, that does not require further processing or purification of the resulting reaction mixture. It is further desirable to improve the yield of the fluorinated sulfinate.

SUMMARY

In one aspect, the description herein provides a process comprising:
a) providing a perfluorovinylether sulfonyl halide represented by the following formula (I):

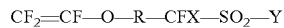

wherein Y is Cl or F, X is F or a linear or branched perfluorinated alkyl group, and R is a linear or branched perfluorinated linking group, which may be saturated or unsaturated, substituted or unsubstituted; and b) reducing the perfluorovinylether sulfonyl halide with a reducing agent in an organic protic solvent, wherein the reducing agent is represented by one of formula (II) and formula (III), wherein formula (II) is:

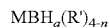

wherein n is 1, 2, 3, or 4, M is an alkali metal, and R' is R'', OR'', OH, or OC(0)R'', wherein R'' is a C1 to C6 linear or branched alkyl group; and or formula (III) is:

wherein x is 0 or 1, y is 1 or 2, z is 3, 4, 5, or 6, and w is 1, 2, or 3.

In some embodiments, the process further comprises the step of adding an acid to produce a perfluorovinylether sulfinic acid. In some embodiments, the process further comprises the step of adding a base to the perfluorovinylether sulfinic acid to produce a perfluorovinylether sulfinic acid salt.

In one aspect, R is selected from: $-(CF_2)_a-$, $-(CF_2)_a-O-(CF_2)_b-$, and $-(CF_2)_a-[O-(CF_2)_b]_c-$, $-[(CF_2)_a-O-]_b-[(CF_2)_c-O-]_d$, and combinations thereof, wherein a, b, c, and d are independently at least 1. In another aspect, the perfluorovinylether sulfonyl halide used in the process of the present invention comprises $CF_2=CF-O-C_4F_8-SO_2F$ and the perfluorovinylether sulfinate formed by the process of the present invention comprises $CF_2=CF-O-C_4F_8-SO_2M'$, wherein M' is hydrogen or an organic or inorganic cation. In another aspect the perfluorovinylether sulfonyl halide used in the process of the present invention comprises $CF_2=CF-O-CF_2CF(CF_3)-O-CF_2CF_2-SO_2F$ and the perfluorovinylether sulfinate formed by the process of the present invention comprises $CF_2=CF-O-CF_2CF(CF_3)-O-CF_2CF_2-SO_2M'$, wherein M' is hydrogen or an organic or inorganic cation. In still another aspect, the perfluorovinylether sulfonyl halide used in the process of the present invention comprises $CF_2=CF-O-CF_2CF_2-SO_2F$ and the perfluorovinylether sulfinate formed by the process of the present invention comprises $CF_2=CF-O-CF_2CF_2-SO_2M'$, wherein M' is hydrogen or an organic or inorganic cation.

In some embodiments of the present invention, the hydride reducing agent is selected from the group comprising $NaBH_4$ and $KBH_4$.

In still another aspect, the step of reducing the perfluorovinylether sulfonyl halide with a reducing agent in an organic protic solvent is performed such that the reducing agent is added to a mixture of the perfluorovinylether sulfonyl halide and the organic protic solvent.

In some embodiments, the solvent is selected from the group comprising a $C_1$-$C_4$ alcohol and a $C_1$-$C_4$ alcohol comprising an ether. In some embodiments, the solvent further comprises at least one cosolvent.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term:

"a", "an", and "the" are used interchangeably and mean one or more; and "and/or" is used to indicate one or both stated cases may occur, for example A and/or B includes, (A and B) and (A or B). Also herein, recitation of ranges by endpoints includes all numbers subsumed within that range (e.g., 1 to 10 includes 1.4, 1.9, 2.33, 5.75, 9.98, etc.). Also herein, recitation of "at least one" includes all numbers of one and greater (e.g., at least 2, at least 4, at least 6, at least 8, at least 10, at least 25, at least 50, at least 100, etc.).

"Sulfinate" is used to indicate both sulfinic acids and sulfinic acid salts. Also herein, "fluorosulfinate" and "fluorinated sulfinate" are used interchangeably to indicate sulfinic acids and sulfinic acid salts which contain at least one fluorine atom.

Perfluorovinyl ether sulfonyl halides useful in the present invention may be represented by formula (I). The perfluorovinyl ether sulfonyl halides may comprise a single perfluorovinyl ether sulfonyl halide compound or a mixture of perfluorovinyl ether sulfonyl halides. In some embodiments, the perfluorinated linking group, R, is a saturated or unsaturated, linear or branched moiety. R can be substituted, for example, one or more substituent groups, or R can be unsubstituted. The perfluorinated linking group can optionally comprise catenary heteroatoms, for example, nitrogen, oxygen, or sulfur atoms that replace one or more carbon atoms of the perfluorinated linking group, R, in a manner such that the heteroatom is bonded to at least two carbon atoms of the perfluorinated linking group. In some embodiments R is selected from: $-(CF_2)_a-$, $-(CF_2)_a-O-(CF_2)_b-$, and $-(CF_2)_a-[O-(CF_2)_b]_c-$, $-[(CF_2)_a-O-]_b-[(CF_2)_c-O-]_d$, and combinations thereof, wherein a, b, c, and d are independently at least 1. In some embodiments, R will have from about 1, 2, 5, or even 7 to about 10, 12, 15, 18, or even 20 carbon atoms.

Exemplary perfluorovinyl ether sulfonyl halides useful in the present invention include:

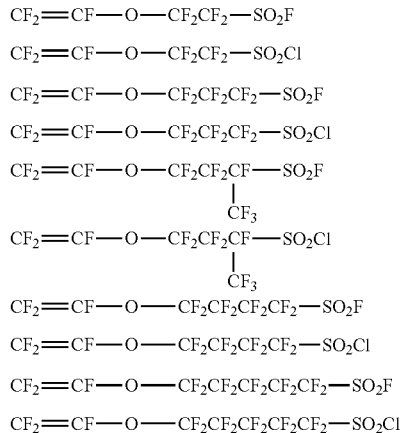
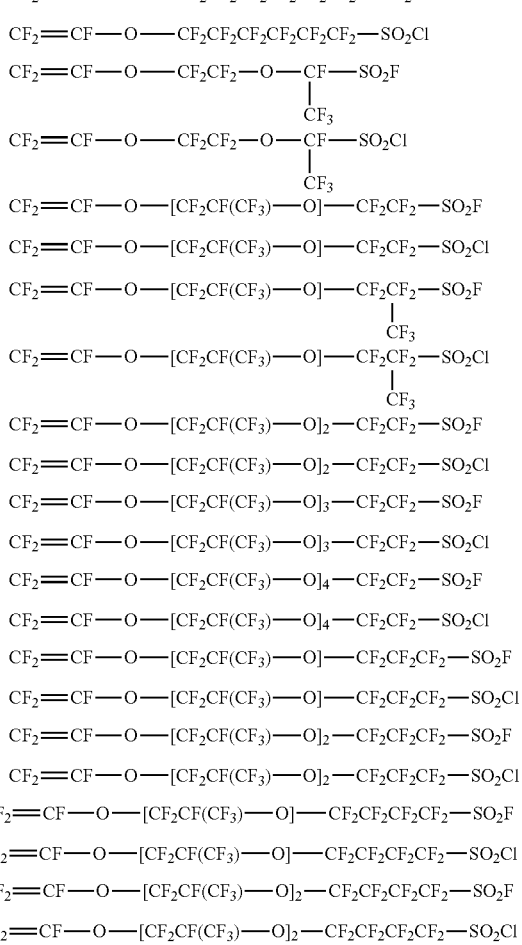

The solvent comprises at least one organic protic solvent. In some embodiments, the solvent may comprise one or more alcohols having a boiling point of 110° C. or less at 760 torr. Exemplary useful organic protic solvents include formic acid, acetic acid, and alcohols. In some embodiments, the solvent will not contain water. Lower alkanols, particularly those having from 1 to 4 carbon atoms, are preferred for use in the process as solvents. In some embodiments the lower alkanols may contain additional oxygen groups, such as a methoxy group. Exemplary useful alcohols include methanol, ethanol, isopropanol, n-butanol, tertiary butanol, isobutanol, methoxyethanol and glycol. In some embodiments, the solvent is ethanol. In some embodiments, the solvent is isopropanol.

In some embodiments, a cosolvent may be present in addition to the at least one organic protic solvent. In some embodiments, the cosolvent may be an additional organic protic solvent. In some embodiments, the cosolvent may be an aprotic solvent. In some embodiments, the cosolvent may include tetrahydrofuran (THF), glyme, dimethylformamide (DMF), diethyl ether, or water.

The solvent should be present in an amount sufficient to allow adequate stirring and heat transfer during the reaction. In some embodiments, the solvent can be removed after completion of the reaction to achieve the desired level of fluorosulfinate product purity. In some embodiments, a cosolvent may be present in an amount up to 90 wt. % of the total combined solvent and cosolvent amount.

Any conventional method may be used to remove the solvent, such as extraction, distillation under reduced pressure, recrystallization, column chromatography, and other known methods of separation.

Reducing agents useful in some embodiments of the present invention include those represented by formula (II): $MBH_n(R')_{4-n}$, wherein n is 1, 2, 3, or 4, M is an alkali metal, and R' is R", OR", OH, or OC(0)R", wherein R" is a C1 to C6 linear or branched alkyl group. In some embodiments, useful hydride reducing agents include sodium borohydride, potassium borohydride, and lithium borohydride. In some embodiments of the present invention, useful reducing agents include those represented by formula (III): $Al_x(B_yH_z)_w$, wherein x is 0 or 1, y is 1 or 2, z is 3, 4, 5, or 6, and w is 1, 2, or 3. Exemplary reducing agents for use in some embodiments of the present invention include $NaBH_4$, $KBH_4$, $NaBH(OCH_3)_3$, $LiBH_4$, $Al(BH_4)_3$, $NaBH_3CN$, $LiBH(CH_3)_3$, $LiBH(CH_2CH_3)_3$, $BH_3$, and $B_2H_6$.

Other useful reducing agents include hydrogen, hydrazine, diisobutyl aluminum hydride, sodium hydride, lithium hydride, potassium hydride, aluminum hydride, calcium hydride, lithium aluminum hydride, mono-, di-, or tri(lower alkoxy) alkali metal aluminum hydrides, mono-, di-, or tri (lower alkoxy lower alkoxy) alkali metal aluminum hydrides, di(lower alkyl) aluminum hydrides, alkalimetalcyanoborohydrides, tri(loweralkyl) tin hydrides, tri(aryl) tin hydrides, and the like.

In some embodiments, the process of the invention is carried out by adding the reducing agent to a perfluorovinyl ether sulfonyl halide-solvent mixture. Alternatively, the process may also be carried out by adding the perfluorovinyl ether sulfonyl halide to a reducing agent-solvent mixture.

In some embodiments, the process of the reducing step is performed in an oxygen-free environment. In some embodiments, the oxygen-free environment can be achieved through the use of nitrogen gas.

In some embodiments the process of the reducing step is carried out using dry, no-moisture solvents that do not contain water.

The reducing agent may be added in an amount such that the ratio of moles of reducing agent to moles of perfluorovinyl ether sulfonyl halide is in the range of at least 0.25, 0.5, 0.75, 1.0, 1.25, 1.5, or even 1.7 to at most 1.8, 1.9, 2.0, or even 3.0. In some embodiments the ratio of moles of reducing agent to moles of perfluorovinyl ether sulfonyl halide is from 1.7 to 1.8. In some embodiments, the ratio of moles of reducing agent to moles of perfluorovinyl ether sulfonyl halide is 1.8.

The temperature of the sulfinic acid, including mixtures of solvent and sulfinic acid, should be maintained under 120° C. to prevent decomposition of the sulfinic group.

In some embodiments, the addition of the reducing agent is performed at a temperature between about −20° C. to about 100° C. For example, the reducing agent can be added while the reaction solution is kept at a temperature of from about −20° C., −10° C., 0° C., or even 10° C. to about 20° C., 40° C., 60° C., 80° C., or even 100° C. In some embodiments, the temperature range for addition of the reducing agent is between 0° C. and 30° C. In some embodiments, the reduction reaction mixture is allowed to warm to room temperature following addition of the reducing agent. In some embodiments, the temperature of the reaction mixture may be maintained at a temperature of from about −20° C., −10° C., 0° C., or even 10° C. to about 20° C., 40° C., 60° C., 80° C., or even 100° C. for the duration of the reaction time.

The addition time of the reducing step may last, in some embodiments, for up to 2 hours, up to 4 hours, or up to 10 hours. In some embodiments the addition time may last longer, for up to 15 hours, up to 20 hours, or even up to 24 hours.

To generate the free perfluorovinyl ether sulfinic acid, an acid may be added immediately following the reduction reaction. In some embodiments, a strong acid, such as hydrochloric acid, nitric acid, or sulfuric acid may be added. In some embodiments, the acid is added when the reaction mixture reaches room temperature, e.g. 23° C. The acid may be added in some embodiments at the end of the desired addition time for the reducing step, such as at 2 hours, 4 hours, 10 hours, 15 hours, 20 hours, or 24 hours after addition of the reducing agent. In some embodiments, the acid is added in an amount sufficient to decrease the pH of the reaction mixture to pH 5, pH 3, or even pH 1.

If desired, the free perfluorovinyl ether sulfinic acid can be converted to the acid salt through the additional step of adding a base. In some embodiments, the base can be an alkali metal hydroxide, for example, sodium hydroxide and potassium hydroxide, or an alkaline earth hydroxide. In some embodiments, the base can be ammonium hydroxide.

In some embodiments, the base is added in an amount sufficient to neutralize the solution. In some embodiments, no excess base is added. The base may be added, in some embodiments, to an aqueous solution of perfluorovinyl ether sulfinic acid to ensure complete titration. Following addition of the base, vacuum stripping may be used to remove water and isolate the neat salt. In some embodiments, the final salt can be diluted with water to make an aqueous solution of the perfluorovinyl ether sulfinic acid salt.

The fluorosulfinate product largely comprises the fluorosulfinate derivatives of the fluoroaliphatic sulfonyl halide(s) used in the reaction mixture. Typically, the fluorosulfinate product will comprise at least about 20, 40, 50, 60, 70, 80, or even 90 weight percent fluorosulfinate compounds, based on the total weight of the fluorosulfinate product.

Exemplary perfluorovinyl ether sulfinates that can be obtained through the process of the present invention include:

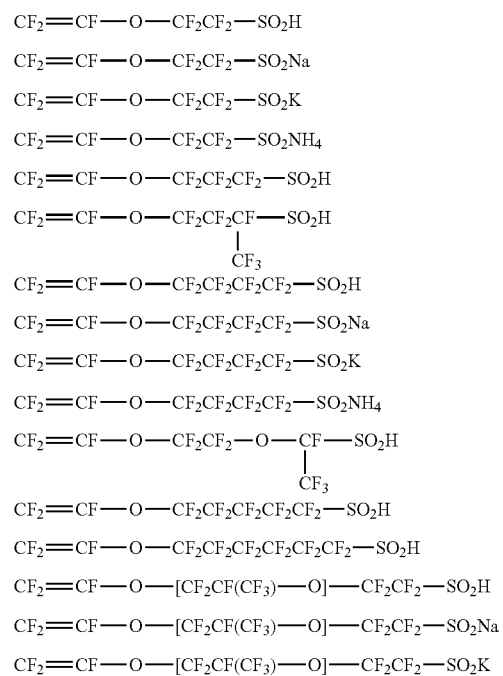

-continued $$CF_2=CF-O-[CF_2CF(CF_3)-O]-CF_2CF_2-SO_2NH_4$$

$$CF_2=CF-O-[CF_2CF(CF_3)-O]-CF_2CF-SO_2H$$
$$\qquad\qquad\qquad\qquad\qquad\qquad | $$
$$\qquad\qquad\qquad\qquad\qquad\qquad CF_3$$

$$CF_2=CF-O-[CF_2CF(CF_3)-O]_2-CF_2CF_2-SO_2H$$

$$CF_2=CF-O-[CF_2CF(CF_3)-O]_3-CF_2CF_2-SO_2H$$

$$CF_2=CF-O-[CF_2CF(CF_3)-O]_4-CF_2CF_2-SO_2H$$

$$CF_2=CF-O-[CF_2CF(CF_3)-O]-CF_2CF_2CF_2-SO_2H$$

$$CF_2=CF-O-[CF_2CF(CF_3)-O]_2-CF_2CF_2CF_2-SO_2H$$

$$CF_2=CF-O-[CF_2CF(CF_3)-O]-CF_2CF_2CF_2CF_2-SO_2H$$

$$CF_2=CF-O-[CF_2CF(CF_3)-O]_2-CF_2CF_2CF_2CF_2-SO_2H$$

Fluoroolefins are useful as comonomers for making fluoropolymers. The fluorinated sulfinate products prepared in accordance with the process of this invention are particularly suitable for initiating a free radical polymerization of ethylenically unsaturated monomers. The fluorinated sulfinate products can be used to initiate the homo- or copolymerization of polymerizable mixtures comprising fluorine-containing ethylenically unsaturated monomer, and optionally, fluorine free, terminally unsaturated monoolefin comonomers (e.g., ethylene or propylene), or iodine- or bromine-containing cure-site comonomers. The polymerization techniques in which the fluorosulfinates of the present invention can be useful typically include emulsion or suspension polymerization in an aqueous medium.

Fluorosulfinates prepared in accordance with the process of the present invention are particularly useful for producing fluoropolymers without ionic ends that benefit the processing of the polymers. Fluorosulfinates produced by the process of the present invention can be used as a surfactant, initiator, reactive intermediate, and reactive monomer to generate unique branched fluoropolymers.

The following embodiments are representatives of the subject matter of the present application:

1. A process for preparing a perfluorovinylether sulfinate comprising:
   a) providing a perfluorovinylether sulfonyl halide represented by the following formula (I):

$$CF_2=CF-O-R-CFX-SO_2-Y$$

wherein Y is Cl or F, X is F or a linear or branched perfluorinated alkyl group, and R is a linear or branched perfluorinated linking group, which may be saturated or unsaturated, substituted or unsubstituted, and optionally comprises catenary heteroatoms; and
   b) reducing the perfluorovinylether sulfonyl halide with a reducing agent in an organic protic solvent, wherein the reducing agent is represented by one of $$MBH_n(R')_{4-n} \qquad \text{formula (II)}$$

wherein n is 1, 2, 3, or 4, M is an alkali metal, and R' is R'', OR'', OH, or OC(O)R'', wherein R'' is a C1 to C6 linear or branched alkyl group;
   or $$Al_x(B_yH_z)_w \qquad \text{formula (III)}$$

wherein x is 0 or 1, y is 1 or 2, z is 3, 4, 5, or 6, and w is 1, 2, or 3.

2. The process according to embodiment 1, wherein the process further comprises the step of adding an acid to produce a perfluorovinylether sulfinic acid.

3. The process according to embodiment 2, wherein the process further comprises the step of adding a base to the perfluorovinylether sulfinic acid to produce a perfluorovinylether sulfinic acid salt.

4. The composition according to any one of the previous embodiments, wherein R is selected from: $-(CF_2)_a-$, $-(CF_2)_a-O-(CF_2)_b-$, and $-(CF_2)_a-[O-(CF_2)_b]_c-$, $-[(CF_2)_a-O-]_b-[(CF_2)_c-O-]_d$, and combinations thereof, wherein a, b, c, and d are independently at least 1.

5. The process according to any one of the preceding embodiments wherein the perfluorovinylether sulfonyl halide comprises $CF_2=CF-O-C_4F_8-SO_2F$ and the perfluorovinylether sulfinate comprises $CF_2=CF-O-C_4F_8-SO_2M'$, wherein M' is hydrogen or an organic or inorganic cation.

6. The process according to any one of the preceding embodiments wherein the perfluorovinylether sulfonyl halide comprises $CF_2=CF-O-CF_2CF(CF_3)-O-CF_2CF_2-SO_2F$ and the perfluorovinylether sulfinate comprises $CF_2=CF-O-CF_2CF(CF_3)-O-CF_2CF_2-SO_2M'$, wherein M' is hydrogen or an organic or inorganic cation.

7. The process according to any one of the preceding embodiments wherein the perfluorovinylether sulfonyl halide comprises $CF_2=CF-O-CF_2CF_2-SO_2F$ and the perfluorovinylether sulfinate comprises $CF_2=CF-O-CF_2CF_2-SO_2M'$, wherein M' is hydrogen or an organic or inorganic cation.

8. The process according to any one of the preceding embodiments wherein the hydride reducing agent is selected from the group comprising $NaBH_4$ and $KBH_4$.

9. The process according to any one of the preceding embodiments wherein the step of reducing the perfluorovinylether sulfonyl halide with a reducing agent in an organic protic solvent is performed such that the reducing agent is added to a mixture of the perfluorovinylether sulfonyl halide and the organic protic solvent.

10. The process according to any one of the preceding embodiments wherein the step of reducing the perfluorovinylether sulfonyl halide with a reducing agent in an organic protic solvent is performed such that the perfluorovinylether sulfonyl halide is added to a mixture of the reducing agent and the organic protic solvent.

11. The process according to any one of the preceding embodiments wherein the solvent is selected from the group comprising a $C_1$-$C_4$ alcohol and a $C_1$-$C_4$ alcohol comprising an ether.

12. The process according to any one of the preceding embodiments wherein the solvent further comprises at least one cosolvent.

EXAMPLES

Advantages and embodiments of this disclosure are further illustrated by the following examples, but the particular materials and amounts thereof recited in these examples, as well as other conditions and details, should not be construed to unduly limit this invention. In these examples, all parts, percentages, proportions, ratios, and the like are by weight unless otherwise indicated. Unless otherwise noted, all reagents were obtained or are available from Aldrich Chemical Co., Milwaukee, Wis., or may be synthesized by known methods.

These abbreviations are used in the following examples: g=gram, min=minutes, cm=centimeter, mm=millimeter, ml=milliliter, and mmHg=millimeters of mercury.

The following examples are merely for illustrative purposes and are not meant to limit in any way the scope of the appended claims.

Materials

| Material | Source |
| --- | --- |
| MV4S | $CF_2$=$CF$—$O$—$C_4F_8$—$SO_2F$, made as described in the Example (Steps A to C) of U.S. Pat. No. 6,624,328 (Guerra) |
| $MV4SO_2H$ | $CF_2$=$CFOC_4F_8SO_2H$, (synthesized as per examples) |
| $MV4SO_2NH_4$ | $CF_2$=$CFOC_4F_8SO_2NH_4$, (synthesized as per example) |
| MV3b2S | $CF_2$=$CFOCF_2CF(CF_3)OCF_2CF_2SO_2F$, available from SynQuest Lab, Alachua FL |
| $MV3b2SO_2H$ | $CF_2$=$CFOCF_2CF(CF_3)OCF_2CF_2SO_2H$, (synthesized as per example) |
| $MV3b2SO_2NH_4$ | $CF_2$=$CFOCF_2CF(CF_3)OCF_2CF_2SO_2NH_4$, (synthesized as per example) |

Comparative Example 1

250 g (0.66 mol) MV4S and 500 g tetrahydrofuran (THF) was added to a 3-neck round bottom flask and the solution was stirred and cooled to 0° C. 47 g (1.2 mol) $NaBH_4$ was added in portions through a solids addition funnel over one hour. No exotherm was observed. The reaction was kept under 10° C. throughout the addition of $NaBH_4$. The bath was removed and the slurry was allowed to warm to 20° C. A very exothermic reaction followed that rose to 71° C. After the reaction was allowed to return to 20° C. 130 g of concentrated sulfuric acid in 650 g water was slowly added to give two phases. The lower fluorochemical phase was vacuum stripped overnight to give 116 g of a slight yellow oil after removing solids by filtration. Nuclear magnetic resonance spectroscopy (NMR) gave the desired $MV4SO_2H$ in 23% yield.

Comparative Example 2

50 g (0.13 mol) MV4S and 120 g of dimethylformamide (DMF) were added to a 1 L 3-neck round bottom flask with stirring and the solution was nitrogen purged and cooled to 0° C. 8.9 g (0.23 mol) $NaBH_4$ was added in portions over one hour with a 5° C. exotherm per portion. The reaction was kept under 13° C. throughout the addition of $NaBH_4$. The flask was allowed to warm to 20° C. and the slurry was stirred for 30 minutes. 50 g concentrated sulfuric acid in 250 g water was added slowly. A one phase solution formed and 150 g methyl t-butyl ether (MTBE) was used to extract a top phase. The top phase was vacuum stripped to remove solvent yielding 48.5 g of reaction mixture. NMR gave very little desired $MV4SO_2H$ product.

Comparative Example 3

50 g (0.13 mol) MV4S and 120 g of reagent grade 1,2-dimethoxyethane (glyme) were placed in a 1 L 3-neck round bottom flask with stirring, nitrogen purged and cooled to 0° C. 8.9 g (0.23 mol) $NaBH_4$ was added in portions over one hour with a 5° C. exotherm per portion. The reaction was kept under 19° C. throughout the addition of $NaBH_4$. The flask was allowed to warm to 20° C. and an exothermic reaction occurred that raised the temperature to 80° C. After the reaction temperature cooled to 20° C., 50 g concentrated sulfuric acid in 250 g water was added slowly. A one phase solution formed and 150 g methyl t-butyl ether (MTBE) was used to extract a top phase. The top phase was vacuum stripped to remove solvent yielding 37.8 g of reaction mixture. NMR gave very little vinyl ether product.

Example 1

50 g (0.13 mol) MV4S and 150 ml of reagent grade ethanol was added to a 1 liter 3-neck round bottom flask. The solution was stirred and cooled to 0° C. 3.4 g (0.09 mol) $NaBH_4$ was added in portions over 30 minutes with a 5° C. exothermic temperature rise per portion. The reaction was kept under 10° C. throughout the addition of $NaBH_4$. The flask was allowed to warm to 20° C. and the slurry was stirred for 30 minutes. 26 g concentrated $H_2SO_4$ in 200 g water was added slowly resulting in a temperature rise to 32° C. A lower fluorochemical phase of 31 g of unreacted MV4S was recovered. The clear top solution was extracted with 110 g methyl-t-butyl ether (MTBE) and vacuum stripped to recover 28 g of a semi-solid material. The semi-solid material still contained some water, ethanol, and salts. NMR gave the desired $MV4SO_2H$ in an 86% yield based on reacted MV4S.

Example 2

Example 2 was run identically to example 1 except that used 180 g ethanol, 8.8 g $NaBH_4$, 50 g concentrated $H_2SO_4$ in 250 mL water and 150 g MTBE. Vacuum stripping of the top phase removed solvent and yielded 88.6 g of concentrated product which was then diluted with water to 156 g. NMR gave the desired $MV4SO_2H$ in a 91% yield.

Example 3

Example 3 was run identically to example 2 except on a larger scale. In place of the amounts used in example 2, example 3 used 251 g (0.66 mol) MV4S, 600 g of ethanol, 44.2 g (1.16 mol) $NaBH_4$, 250 g concentrated $H_2SO_4$ in 1250 mL water and 500 g MTBE. Vacuum stripping of the top phase removed solvent and yielded 380 g of concentrated product after filtration of solids which was then diluted with water to 786 g. NMR gave the desired $MV4SO_2H$ in an 89% yield.

Example 4

Example 4 was run identically to example 3 except in place of the amounts used in example 3, example 4 used 255 g (0.67 mol) MV4S and 44 g (1.15 mol) $NaBH_4$. This example demonstrates the salt formation. Vacuum stripping of the top phase removed solvent and yielded 212 g of concentrated product after filtration of solids. NMR gave the desired $MV4SO_2H$ in an 81% yield.

Addition of 20 g (0.32 mol) ammonia (as 27% ammonium hydroxide) to 110 g of $MV4SO_2H$ gave a quantitative yield of $MV4SO_2NH_4$ as a waxy solid. A melting point of 74° C. was measured for $MV4SO_2NH_4$.

Example 5

100 g (0.26 mol) $CF_2$=$CFOC_4F_8SO_2F$, MV4S and 220 g of absolute ethanol was added to a 1 L 3-neck round bottom flask with stirring and nitrogen purged at 20° C. A charge of 17.7 g (0.46 mol) $NaBH_4$ was added in portions over one hour with the exotherm kept at 50° C. The reaction mixture was foamy with a slight reflux. The reaction was allowed to return to 20° C. and 100 g concentrated $H_2SO_4$ in 400 g water was added. A slight opaque one phase solution formed and 182 g MTBE was used to extract a top phase. Vacuum stripping of the top phase removed solvent and gave 118 g of concentrated product after filtration of solids. NMR gave the desired $MV4SO_2H$ in a 72% yield.

Example 6

54 g (0.14 mol) MV4S and 110 g of 2-propanol was added to a 1 L 3-neck round bottom flask with stirring, nitrogen purged and cooled to 0° C. 9.6 g (0.25 mol) NaBH$_4$ was added in portions over one hour with the reaction temperature allowing to reach 36° C. The flask was allowed to return to 20° C. and the slurry was stirred for 30 minutes. Addition of 50 g concentrated H$_2$SO$_4$ in 200 g water was added slowly. A slight opaque one phase solution formed and 100 g MTBE was used to extract a top phase. Vacuum stripping of the top phase removed solvent and gave 36 g of concentrated product after filtration of solids. NMR gave the desired MV4SO$_2$H in a 57% yield.

Example 7

51.5 g (0.14 mol) MV4S and 110 g of anhydrous methanol was added to a 1 L 3-neck round bottom flask with stirring, nitrogen purged and cooled to 0° C. Addition of 9.2 g (0.24 mol) NaBH$_4$ was added in portions over one hour with a 5° C. exothermic temperature rise per portion. The reaction was kept under 10° C. throughout the addition of NaBH$_4$. The flask was allowed to warm to room temperature and the slurry was stirred for 30 minutes. Addition of 50 g concentrated H$_2$SO$_4$ in 200 g water was added slowly. A slight opaque one phase solution formed and 100 g MTBE was used to extract a top phase. Vacuum stripped of the top phase removed solvent and gave 36 g of concentrated product after filtration of solids. NMR gave the desired MV4SO$_2$H in a 66% yield.

Example 8

52.4 g (0.14 mol) MV4S and 110 g of reagent grade 1-butanol was added to a 1 L 3-neck round bottom flask with stirring and nitrogen purged. 9.3 g (0.24 mol) NaBH$_4$ was added in portions over one hour with the reaction temperature allowing to go to 50° C. The flask was allowed to reach room temperature and the slurry was stirred for 30 minutes. Addition of 50 g concentrated H$_2$SO$_4$ in 200 g water was added slowly. Two phases were obtained with the product and solvent in the top phase. Vacuum stripped of the top phase removed solvent and gave 49.6 g of concentrated product after filtration of solids. NMR gave the desired MV4SO$_2$H in a 60% yield.

Example 9

45 g (0.10 mol) MV3b2S and 180 g of reagent grade ethanol was added to a 1 L 3-neck round bottom flask with stirring, nitrogen purged and cooled to 0° C. Addition of 6.9 g (0.18 mol) NaBH$_4$ was added in portions over 30 minutes with a 5° C. exothermic temperature rise per portion. The reaction was kept under 10° C. throughout the addition of NaBH$_4$. The flask was allowed to warm to 20° C. and the slurry was stirred for 30 minutes. 50 g concentrated H$_2$SO$_4$ in 250 g water was added slowly. A slight opaque one phase solution formed and 150 g MTBE was used to extract a top phase. Vacuum stripping of the top phase removed solvent and gave 20 g of concentrated product after filtration of solids for a 51% crude yield. NMR gave the desired MV3b2SO$_2$H.

Example 10

Addition of 2.2 g (0.03 mol) ammonia (as 27% ammonium hydroxide) to 10 g of MV3b2SO$_2$H from example 9 gave a quantitative yield of MV3b2SO$_2$NH$_4$ as a waxy solid. No melting point for MV3b2SO$_2$NH$_4$ was observed and onset of decomposition occurred at 208° C.

Example 11

17.7 g (0.46 mol) NaBH$_4$ and 218 g of reagent grade ethanol was placed in a 1 L 3-neck round bottom flask with stirring, nitrogen purged and cooled to 0° C. 100 g (0.26 mol) MV4S was added over two hours with the reaction temperature kept under 10° C. The reaction was warmed to 20° C. and stirred for one-half an hour followed by addition of 100 g concentrated sulfuric acid in 400 g water. A one phase solution formed and 200 g MTBE was used to extract a top phase. The top phase was vacuum stripped to remove solvent yielding 75 g of concentrated product after filtration of solids. NMR gave the desired MV4SO$_2$H in a 43% yield.

Example 12

10 g MV4S (26.3 mmol), 20 g dried THF (distilled from CaH$_2$) and 5 g absolute ethanol were charged into a 250 ml 3-neck round bottom flask fitted with a thermometer, reflux condenser, nitrogen flow and a solid-addition funnel. The solution was cooled to 0° C. under nitrogen and 1.32 g NaBH$_4$ (34.9 mmol) was added in portions with stirring over 30 minutes keeping the temperature below 10° C. After addition the solution was allowed to slowly warm up to 20° C. under nitrogen. $^{19}$F NMR analysis of the reaction mixture indicated 92% conversion of —SO$_2$F after reaction at 20° C. for 15 minutes and 100% conversion after 30 minutes. The chemical shift of —SO$_2$F at +42 ppm disappeared and the signal of —CF$_2$SO$_2$F at −111 ppm was shifted to −135 ppm for the corresponding —CF$_2$SO$_2$Na product. Based on the signal of —CF$_2$SO$_2$Na at −135 ppm and the signal of CF$_2$=CFO—, an NMR yield of >95% of the desired product, CF$_2$=CF—O—C$_4$F$_8$—SO$_2$Na, was identified. No hydride by-product was observed.

Example 13

10 g MV4S (26.3 mmol), 24 g dried THF (distilled from CaH$_2$) and 4.0 g acetic acid (obtained from EM Science, Gibbstown, N.J., >99.5%) were charged into a 250 ml 3-neck round bottom flask fitted with a thermometer, reflux condenser, nitrogen flow and a solid-addition funnel. The solution was cooled below 10° C. under nitrogen and 0.85 g NaBH$_4$ (34.9 mmol) was added in portions with stirring over 30 minutes keeping the temperature below 10° C. After addition the solution was allowed to slowly warm up to 20° C. under nitrogen and stirring was continued for 30 minutes. $^{19}$F NMR analysis showed 36% conversion of —SO$_2$F to —SO$_2$Na with high selectivity. Another 0.5 g NaBH$_4$ (13.2 mmol) was added and reacted at 20° C. for another 1 hour and the conversion increased to 50%. The conversion was further increased to 94% when another 0.42 g NaBH4 was added at 20° C. and reacted for an additional one hour. The final ratio of CF$_2$=CF—O—C$_4$F$_8$—SO$_2$Na and hydride by-product was 96 to 4.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A process comprising:
   a) providing a perfluorovinylether sulfonyl halide represented by the following formula (I):

$$CF_2=CF-O-R-CFX-SO_2-Y$$

wherein Y is Cl or F, X is F or a linear or branched perfluorinated alkyl group, and R is a linear or branched perfluorinated linking group, which may be saturated or unsaturated, substituted or unsubstituted; and
   b) reducing the perfluorovinylether sulfonyl halide with a reducing agent in an organic protic solvent to provide a perfluorovinylether sulfinate, wherein the reducing agent is represented by one of formula (II) and formula (III), wherein
   formula (II) is:

$$MBH_n(R')_{4-n}$$

wherein n is 1, 2, 3, or 4, M is an alkali metal, and R' is R", OR", OH, or OC(O)R", wherein R" is a C1 to C6 linear or branched alkyl group; and
   or
   formula (III) is:

$$Al_x(B_yH_z)_w$$

wherein x is 0 or 1, y is 1 or 2, z is 3, 4, 5, or 6, and w is 1, 2, or 3.

2. The process according to claim 1, wherein the process further comprises adding an acid to the perfluorovinylether sulfonyl halide to produce a perfluorovinylether sulfinic acid.

3. The process according to claim 2, wherein the process further comprises adding a base to the perfluorovinylether sulfinic acid to produce a perfluorovinylether sulfinic acid salt.

4. The composition claim 1, wherein R is selected from: $-(CF_2)_a-$, $-(CF_2)_a-O-(CF_2)_b-$, and $-(CF_2)_a-[O-(CF_2)_b]_c-$, $-[(CF_2)_a-O-]_b-[(CF_2)_c-O-]_d$, and combinations thereof, wherein a, b, c, and d are independently at least 1.

5. The process according to claim 1 wherein the perfluorovinylether sulfonyl halide comprises $CF_2=CF-O-C_4F_8-SO_2F$ and the perfluorovinylether sulfinate comprises $CF_2=CF-O-C_4F_8-SO_2M'$, wherein M' is hydrogen or an organic or inorganic cation.

6. The process according to claim 1 wherein the perfluorovinylether sulfonyl halide comprises $CF_2=CF-O-CF_2CF(CF_3)-O-CF_2CF_2-SO_2F$ and the perfluorovinylether sulfinate comprises $CF_2=CF-O-CF_2CF(CF_3)-O-CF_2CF_2-SO_2M'$, wherein M' is hydrogen or an organic or inorganic cation.

7. The process according to claim 1 wherein the perfluorovinylether sulfonyl halide comprises $CF_2=CF-O-CF_2CF_2-SO_2F$ and the perfluorovinylether sulfinate comprises $CF_2=CF-O-CF_2CF_2-SO_2M'$, wherein M' is hydrogen or an organic or inorganic cation.

8. The process according to claim 1 wherein the hydride reducing agent is selected from the group comprising $NaBH_4$ and $KBH_4$.

9. The process according to claim 1 wherein reducing the perfluorovinylether sulfonyl halide with a reducing agent in an organic protic solvent is performed such that the reducing agent is added to a mixture of the perfluorovinylether sulfonyl halide and the organic protic solvent.

10. The process according to claim 1 wherein reducing the perfluorovinylether sulfonyl halide with a reducing agent in an organic protic solvent is performed such that the perfluorovinylether sulfonyl halide is added to a mixture of the reducing agent and the organic protic solvent.

11. The process according to claim 1 wherein the organic protic solvent is selected from the group comprising a $C_1$-$C_4$ alcohol and a $C_1$-$C_4$ alcohol comprising an ether.

12. The process according to claim 1 wherein the organic protic solvent further comprises at least one co-solvent.

* * * * *

UNITED STATES PATENT AND TRADEMARK OFFICE
CERTIFICATE OF CORRECTION

PATENT NO. : 8,907,125 B2
APPLICATION NO. : 13/994967
DATED : December 9, 2014
INVENTOR(S) : Miguel Guerra et al.

It is certified that error appears in the above-identified patent and that said Letters Patent is hereby corrected as shown below:

On the Title Page, Item 56

Line 4 (Other Publications), Delete "polyfluoroalky" and insert -- polyfluoroalkyl --, therefor.
Line 20 (Other Publications), Delete "α 107-dibromides"," and insert -- α ω-dibromides", --, therefor.
Line 26 (Other Publications), Delete "methane-,-octane-," and insert -- methane-, - octane-, --, therefor.

In the Specification

Column 2
Line 20, Delete "$MBH_a(R')_{4-n}$" and insert -- $MBH_n(R')_{4-n}$ --, therefor.
Line 22, Delete "OC(0)R"," and insert -- OC(O)R", --, therefor.

Column 5
Line 8, Delete "OC(0)R"," and insert -- OC(O)R", --, therefor.

Column 12
Line 52, Delete "NaBH4" and insert -- $NaBH_4$ --, therefor.

In the Claims

Column 13
Line 36, Delete "composition" and insert -- "process" --, therefor.

Signed and Sealed this
Twenty-first Day of July, 2015

Michelle K. Lee
*Director of the United States Patent and Trademark Office*